(12) United States Patent
Morita et al.

(10) Patent No.: US 8,488,738 B2
(45) Date of Patent: Jul. 16, 2013

(54) RADIOGRAPHIC APPARATUS

(75) Inventors: Hisanori Morita, Kyoto (JP); Kimihiro Takahama, Chofu (JP)

(73) Assignee: Shimadzu Corporation, Kyoto (JP)

( * ) Notice: Subject to any disclaimer, the term of this patent is extended or adjusted under 35 U.S.C. 154(b) by 272 days.

(21) Appl. No.: 12/979,518

(22) Filed: Dec. 28, 2010

(65) Prior Publication Data
US 2011/0164725 A1 Jul. 7, 2011

(30) Foreign Application Priority Data

Jan. 6, 2010 (JP) .................................. 2010-001090
Feb. 19, 2010 (JP) .................................. 2010-034554

(51) Int. Cl.
*A61B 6/00* (2006.01)

(52) U.S. Cl.
USPC ........................................................... 378/62

(58) Field of Classification Search
USPC ..................... 378/8, 62, 68, 69, 95
See application file for complete search history.

(56) References Cited

U.S. PATENT DOCUMENTS

2005/0201510 A1 * 9/2005 Mostafavi ........................ 378/8

FOREIGN PATENT DOCUMENTS

JP 2004-57559 A 2/2004

* cited by examiner

*Primary Examiner* — Irakli Kiknadze
(74) *Attorney, Agent, or Firm* — Cheng Law Group, PLLC (57) ABSTRACT

A radiographic apparatus includes a radiation source for emitting radiation, a radiation source control unit for instructing the radiation source to emit the radiation, and a radiation detector for detecting the radiation. The radiation detector outputs real-time detection data when the radiation source emits the radiation intermittently or continuously, and outputs quiescence detection data when the radiation source emits still radiation. The quiescence detection data is acquired by the radiation source control unit controlling the radiation source to start emitting the radiation at a time earlier than a predicted point of time by a predetermined time calculated based on an estimated irradiation time.

20 Claims, 6 Drawing Sheets

RADIOGRAPHIC APPARATUS

BACKGROUND OF THE INVENTION (1) Field of the Invention

This invention relates to a radiographic apparatus having a radiation source and a radiation detector, and more particularly to a radiographic apparatus, which can radiograph the lung field and abdomen, and carry out a subtraction process for emphasizing bone tissues and soft tissues.

(2) Description of the Related Art

A radiographic apparatus is installed in a medical institution for acquiring radiological images of patients. Such a radiographic apparatus has a radiation source for emitting radiation, and a radiation detector for detecting the radiation (Japanese Unexamined Patent Publication No. 2004-057559, for example).

A construction of a conventional radiographic apparatus will be described. A conventional radiographic apparatus includes a radiation source, a radiation detector, an image generating unit and a superimposing unit. Such radiographic apparatus is constructed to carry out two radiographing operations to generate a single subtraction image based on a difference between the two fluoroscopic images obtained from the radiographing operations.

The output energy of the radiation source is different between the first radiographing operation and second radiographing operation. The radiation source provides a high energy output for the first radiographing operation, and a low energy output for the second radiographing operation. In both operations, images of bone tissue and soft tissue of the patient are acquired.

In the first radiographing operation, the degree of radiation transmission is different between the bone tissue and soft tissue. In the second radiographing operation also, the degree of radiation transmission is different between the bone tissue and soft tissue. And there is no agreement between the way in which the radiation transmission is different in the first radiographing operation and that in the second radiographing operation. There occurs a phenomenon in which, for example, although the first radiographing operation with the high energy radiation produces a considerable difference in pixel value between a portion of bone tissue and a portion of soft tissue, the second radiographing operation with the low energy radiation produces little difference in pixel value between the portion of bone tissue and the portion of soft tissue. When a difference is determined between the two images having such characteristics, a subtraction image emphasizing the bone tissue can be acquired, with the portions of soft tissue reflected in the two images canceled, and the portions of bone tissue appearing more clearly.

When the two images are superimposed after a tone correction, a subtraction image showing the portion of soft tissue more clearly can be acquired.

A conventional radiographic apparatus for radiographing the chest and abdomen includes a radiation source, a radiation detector and an image generating unit. Such radiographic apparatus is constructed to carry out still image radiography by emitting still (single-shot) radiation to generate still images showing the lung field of a patient.

The lungs of the patient always continue moving due to respiration of the patient. For observing the lungs, it is desirable to carry out still image radiography in a state of maximum lung expansion. Then, at a time of radiography, the patient is instructed to inhale air and suspend respiration temporarily in that state.

For observing the abdomen, it is desirable to carry out still image radiography in a state of maximum lung contraction. Then, at a time of radiography, the patient is instructed to exhale air and suspend respiration temporarily in that state.

However, the conventional radiographic apparatus have the following problems.

The conventional radiographic apparatus has a problem that the patient can move during the time between the first radiographing operation and the next radiographing operation, thereby blurring a subtraction image. When there is a difference between a patient's position imaged in the first radiographing operation and a patient's position imaged in the second radiographing operation, a subtraction image will be acquired from a superimposition of the images having the patient's positions shifted from each other. Therefore, the subtraction image acquired will become blurred.

Even if the patient is instructed not to move at the time of radiography, the interior of the patient constantly keeps moving due the patient's heartbeat. When radiography is carried out without considering this movement, a clear subtraction image cannot be acquired.

Then, conventionally, a heart rate is checked by electrocardiography to grasp the cycles of the interior of the patient assuming the same shape, and radiography is carried out for each cycle. That is, a first radiographing operation is started when the heart expands to the full, and a second radiographing operation is started when the heart is in the same state again.

A subtraction image acquired by such a method is blurred also. This is because, when compared at the end of each radiographing operation, the states of the heart are not in agreement. According to the conventional construction, the first and second radiographing operations are the same only in the timing of starting radiation emission, and there is no guarantee that the first and second radiographing operations are carried out when the heart is in the same shape.

The conventional radiographic apparatus needs electrocardiographic measurement, and its operation is complicated. Such construction is not desirable for a large medical institution, for example, where many fluoroscopic images must be acquired with a single apparatus.

The radiographic apparatus for radiographing the chest and abdomen has a problem that it cannot perform radiography suited to the purposes of examination when radiographing patients unable to cope with instructions on respiration of the patient, such as infants, old patients, and patients with artificial respirators.

When such a patient cannot be radiographed in a state of suspending respiration, the operator needs to carry out still image radiography by choosing the right timing of respiration of the patient. That is, the operator visually observes a swelling of the body surface of the patient, and carries out still image radiography at the moment of the patient finishing inhalation or exhalation.

Still images acquired in such a state cannot necessarily be said ideal for diagnosis. It is difficult to recognize visually an inhaling state of the patient. In addition, it is difficult to operate the radiographic apparatus to take a still image immediately after the operator decides to carry out radiography. An expanding state of the lungs at the time of radiography is not necessarily a desired one.

There is a conventional construction which can carry out still image radiography synchronously with respiration by using a distance sensor for monitoring approach and withdrawal of the chest of a patient. With this construction, however, it is difficult to grasp the cycle of respiration accurately when the patient wears thick clothes or when the respiration of the patient is weak. After all, a situation will occur where a swelling state of the lungs at the time of radiography is not a desired on.

Unless a swelling state of the lungs is constant at the time of radiography, a problem will arise when observing variations in the disease condition of the patient. That is, since the swelling state of the lungs of the patient is different for each examination, it will be unclear whether the difference between still images upon comparison is due to variations in the disease condition or the difference is due to a difference in the swelling state of the lungs.

This invention has been made having regard to the state of the art noted above, and its object is to provide a radiographic apparatus which can acquire clear images in a simple way.

SUMMARY OF THE INVENTION

In order to fulfill the above object, this invention provides the following construction.

A first radiographic apparatus, according to this invention, has a radiation source for emitting radiation, a radiation source control device for instructing the radiation source to emit the radiation, and a radiation detecting device for detecting the radiation, the radiation detecting device outputting real-time detection data when the radiation source emits the radiation intermittently or continuously, and outputting quiescence detection data when the radiation source emits still radiation, the radiographic apparatus comprising a storage device for storing a required transit dose indicating what dose of the radiation transmitted through a patient is required for acquisition of the quiescence detection data; a time predicting device for predicting, based on a cycle of variation of a dynamic part which cyclically changes in size in the patient, a point of time when the dynamic part of the patient will be in a predetermined state, as a predicted point of time; an irradiation time estimating device for estimating an irradiation time of the radiation at a time of acquiring the quiescence detection data, as an estimated irradiation time, from the real-time detection data and the required transit dose; an image generating device for generating still images based on the quiescence detection data; and an image superimposing device for superimposing still images picked up at different points of time to create a superimposition image; wherein the quiescence detection data is acquired by the radiation source control device controlling the radiation source to start emitting the radiation at a time earlier than the predicted point of time by a predetermined time calculated based on the estimated irradiation time.

According to the construction of this invention in the above radiographic apparatus, real-time radiography is first carried out with a low dose to acquire the real-time detection data, and then still image radiography for diagnosis is carried out with a high dose to acquire the quiescence detection data. The real-time radiography is carried out as preparation to determine radiographic conditions for the still image radiography. In the real-time radiography, a point of time when the dynamic part of the patient will be in a predetermined state is predicted, and radiation irradiation times for the still image radiography are estimated. The point of time is predicted by the time predicting device. The irradiation times are estimated by the irradiation time estimating device.

In the still image radiography, an irradiation with the radiation is started at a time earlier than a predicted point of time by a half of an estimated irradiation time. By choosing this process, the irradiation with the radiation at the time of still image radiography ends at a point of time when the dynamic part of the patient is in a predetermined state. With such still image radiography repeated a plurality of times, the dynamic part of the patient will be reflected in the same shape on the still images acquired. These images may be superimposed together to acquire an image without a blur due to movement of the dynamic part of the patient.

Preferably, the above first radiographic apparatus further comprises a cycle acquiring device for acquiring the cycle of variation of the dynamic part based on the real-time detection data.

With this construction, the cycle of variation of the dynamic part is acquired based on the real-time detection data. Thus, the cycle of the dynamic part can be acquired with increased accuracy.

In the above first radiographic apparatus, it is preferred that the image superimposing device is arranged to create a subtraction image by acquiring a difference between still images picked up under conditions of different energy outputs of the radiation source.

With this construction, a subtraction image is obtained by acquiring a difference between the still images. Thus, a subtraction image emphasizing bone tissue or soft tissue of the patient can be acquired.

Preferably, the above first radiographic apparatus further comprises a histogram analyzing device for carrying out a histogram analysis of the real-time detection data; wherein the cycle acquiring device is arranged to acquire the cycle by comparing histograms sequentially outputted from the histogram analyzing device.

This construction creates histograms of the real-time detection data. The cycle acquiring device can recognize the cycle of the dynamic part such as a body organ conveniently by comparing particular regions of the histograms in real time.

In the above first radiographic apparatus, it is preferred that the dynamic part of the patient is variable by heartbeat.

This construction can inhibit blurring of images due to the heartbeat of the patient. This is because the cyclicity of the dynamic part is due to the heartbeat of the patient, and timing of the still image radiography is set to this cyclicity.

In the above first radiographic apparatus, it is preferred that the dynamic part of the patient comprises the heart.

This construction points to a specific construction of the radiographic apparatus. That is, the dynamic part of the patient comprises the heart. This can inhibit blurring of the heart reflected on the still images superimposed.

In the above first radiographic apparatus, it is preferred that the dynamic part of the patient comprises the lungs.

This construction points to a specific construction of the radiographic apparatus. That is, the dynamic part of the patient comprises the lungs. This can inhibit blurring of the lung field reflected on the still images superimposed.

In the above first radiographic apparatus, it is preferred that the cycle acquiring device is arranged to determine the cycle to be a time taken from a point of time when a state of respiration of the patient is in a specific state and a state of heartbeat of the patient is in a specific state, to a point of time when the state of respiration of the patient is in the same specific state as before and the state of heartbeat of the patient is in the same specific state as before.

According to above constriction, even if the patient has a plurality of dynamic parts with different cyclicities, the above construction can inhibit blurring of the dynamic parts reflected on the still images superimposed. That is, a cycle is determined to be a time taken from a point of time when the state of respiration of the patient is in a specific state and the state of heartbeat of the patient is in a specific state, to a point of time when the state of respiration of the patient is in the same specific state as before again and the state of heartbeat of the patient is in the same specific state as before again. Consequently, whenever still images are picked up, the lung field and the heart are reflected in the same shape and position on the still images.

In the above first radiographic apparatus, it is preferred that the cycle acquiring device is arranged to acquire the cycle by obtaining, from the real-time detection data, one of an area of the dynamic part, a position of the dynamic part, a shape of the dynamic part, and a radiation detection value in a specific location in an image which belongs to the dynamic part at certain times and does not at other times.

The above construction represents various modes of the radiographic apparatus. The cycle acquiring device can acquire the cycle based on variations in the area of the dynamic part such as a body organ, variations in the position of the dynamic part such as a body organ, variations in the shape of the dynamic part such as a body organ, or a radiation detection value in a specific location.

In the above first radiographic apparatus, it is preferred that the cycle acquiring device is arranged to acquire the cycle by obtaining variations with time of the dynamic part, and calculating rates of the variations.

The above construction represents various modes of the radiographic apparatus. The cycle acquiring device constructed as above can acquire the cycle with increased reliability.

A second radiographic apparatus, according to this invention, has a radiation source for emitting radiation to a patient, a radiation source control device for instructing the radiation source to emit the radiation, and a radiation detecting device for detecting the radiation transmitted through the patient, and outputting detection data, the radiographic apparatus comprising a cycle acquiring device for detecting cyclic variations in size of a body organ of the patient; wherein the radiation source is arranged to emit the radiation by determining a point of time for starting emission of the radiation based on a cycle detected by the cycle acquiring device.

According to the construction of this invention, a point of time for starting emission of the radiation is determined according to variations in size of the body organ of the patient. With this arrangement, even if the patient is constantly in motion due to respiration of the patient, for example, the patient will always be radiographed at predetermined times. Thus, since the timing of radiography is determined taking the actual cycle of the body organ into consideration according to this invention, still image radiography of the body organ of the patient in a desired expanded state. That is, two still images picked up at different times may be compared in order to observe variations of a disease condition of the patient, thereby to recognize variations of the disease condition properly.

In the above second radiographic apparatus, it is preferred that the radiation detecting device is arranged to output real-time detection data when the radiation source emits the radiation intermittently or continuously, and the cycle acquiring device is arranged to acquire a cycle of variations of the body organ based on the real-time detection data.

With this construction, the cycle of variation of the body organ of the patient is acquired based on the real-time detection data. Thus, the cycle of the body organ of the patient can be acquired with increased accuracy.

The above second radiographic apparatus may further comprise the histogram analyzing device noted hereinbefore. This will provide the same advantage as described hereinbefore in connection with the first radiographic apparatus.

Preferably, the above second radiographic apparatus further comprises an image generating device for generating images based on the detection signals; wherein the cycle acquiring device is arranged to acquire the cycle by obtaining, from the real-time detection data, one of an area of the body organ, a position of the body organ, a shape of the body organ, and a radiation detection value in a location in an image which belongs to the body organ at certain times and does not at other times.

The above construction represents various modes of the radiographic apparatus. The cycle acquiring device can acquire the cycle based on variations in the area of the body organ of the patient, variations in the position of the body organ of the patient, variations in the shape of the body organ of the patient, or a radiation detection value in a specific location.

In the above second radiographic apparatus, it is preferred that the cycle acquiring device is arranged to acquire the cycle by obtaining variations with time of the lungs of the patient, and calculating rates of the variations.

The above construction represents various modes of the radiographic apparatus. The cycle acquiring device constructed as above can acquire the cycle with increased reliability.

Preferably, the above second radiographic apparatus is constructed for radiographing one of the chest and the abdomen of the patient.

The above construction represents a specific mode of the radiographic apparatus. When the radiographic apparatus radiographs the chest or abdomen of the patient, an expanded state of the lungs of the patient is the same for each time of radiography, thereby to acquire still images well suited for comparison and diagnosis.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A radiographic apparatus according to Embodiment 1 will be described. X-rays in the following description are an example of radiation.

Figure 1:
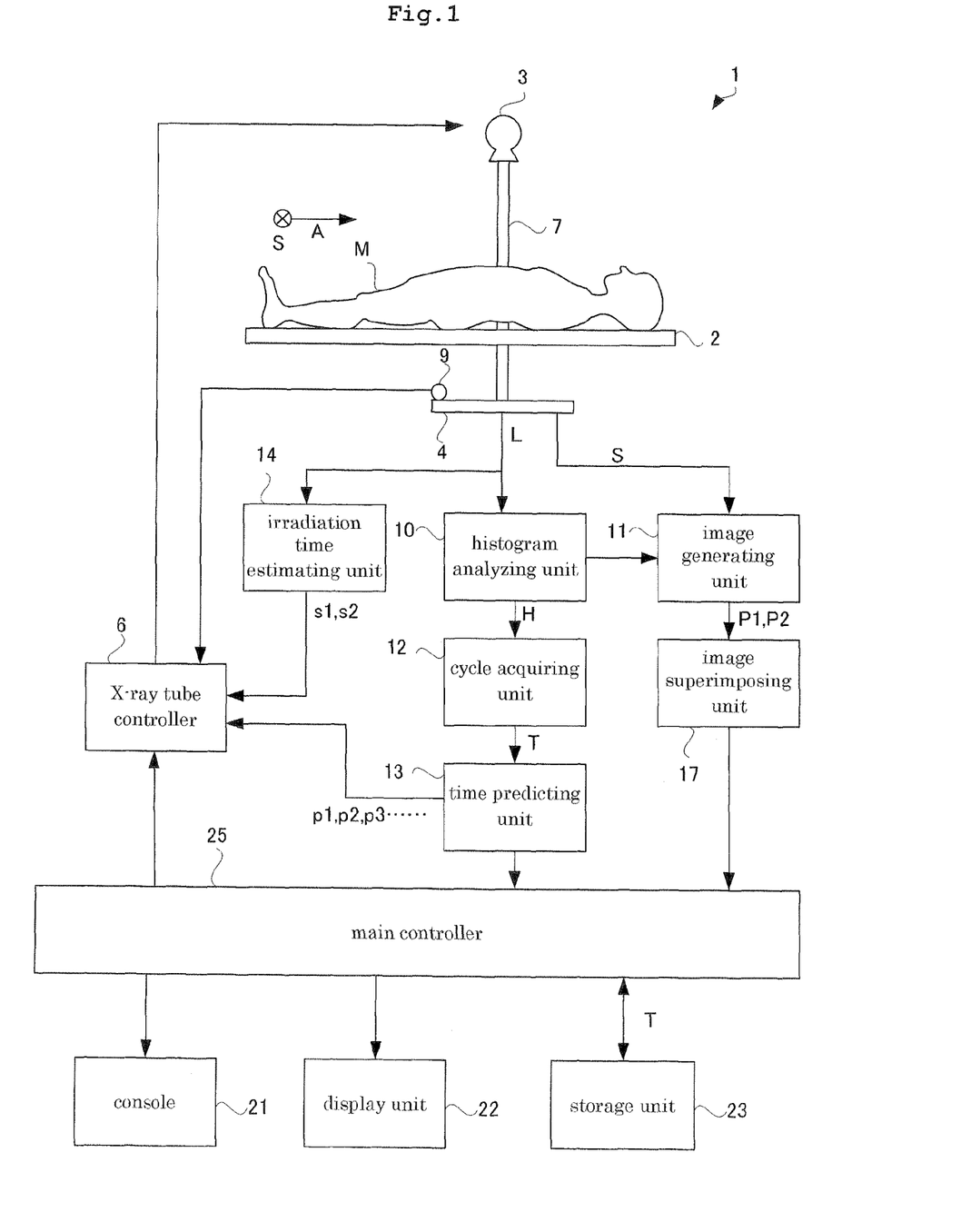
FIG. 1 is a functional block diagram illustrating a construction of an X-ray apparatus according to Embodiment 1.

As shown in FIG. 1, an X-ray apparatus 1 includes a top board 2 for supporting a patient M, an X-ray tube 3 for emitting X-rays to the patient M, an X-ray tube controller 6 for controlling output of the X-ray tube 3, an FPD 4 for detecting X-rays transmitted through the patient M and outputting real-time detection data L and quiescence detection data S, a histogram analyzing unit 10 for conducting a histogram analysis of the real-time detection data L, and an image generating unit 11 for processing the quiescence detection data S and outputting still images P1 and P2. The histogram analyzing unit 10 corresponds to the histogram analyzing device in this invention. The X-ray tube controller 6 corresponds to the radiation source control device in this invention. The X-ray tube 3 corresponds to the radiation source in this invention. The FPD 4 corresponds to the radiation detecting device in this invention. The image generating unit 11 corresponds to the image generating device in this invention.

A strut 7 is provided to support the X-ray tube 3 and FPD 4 en bloc, to be movable along the body axis of the patient M. Consequently, the X-ray tube 3 and FPD 4, while maintaining a positional relationship with each other, move relative to the patient M. A phototimer 9 is disposed on an X-ray detecting plane of the FPD 4, for instructing the X-ray tube controller 6 to end X-ray emission.

The X-ray apparatus 1 has a real-time mode for carrying out real-time radiography at a predetermined frame rate, and a still image acquiring mode for acquiring still images by emitting still radiation to the patient M. In the real-time mode, the X-ray tube 3 emits X-ray beams intermittently at predetermined intervals toward the patient M, and the FPD 4 detects X-rays transmitted through the patient M every time, and outputs real-time detection data L obtained to the histogram analyzing unit 10 and an irradiation time estimating unit 14. In the still image acquiring mode, on the other hand, the X-ray tube 3 emits a single X-ray beam toward the patient M, and the FPD 4 detects X-rays transmitted through the patient M and outputs quiescence detection data S obtained to the image generating unit 11.

In the real-time mode, the histogram analyzing unit 10 conducts a histogram analysis of the real-time detection data L whenever the real-time detection data L is received, and generates histograms H representing a relationship between detection value and frequency of the real-time detection data. The real-time detection data L is sent also to the image generating unit 11 to be converted into dynamic images which are sequentially displayed on a display unit 22 described hereinafter. Thus, the operator can check fluoroscopic states of the patient M by means of the dynamic images in real time.

The histograms H are sent to a cycle acquiring unit 12. The cycle acquiring unit 12, a time predicting unit 13 and the irradiation time estimating unit 14 are provided to determine timing of radiation emission from the X-ray tube 3. Details of operation of these components will be described hereinafter. An image superimposing unit 17 acquires a subtraction image by obtaining a difference between two still images P1 and P2. The cycle acquiring unit 12 corresponds to the cycle acquiring device in this invention.

The X-ray apparatus 1 according to Embodiment 1 further includes a main controller 25 for generally controlling the X-ray tube controller 6, and the display unit 22 which displays X-ray images. This main controller 25 is constructed of a CPU which, by executing various programs, realizes the X-ray tube controller 6, histogram analyzing unit 10, image generating unit 11, cycle acquiring unit 12, time predicting unit 13, irradiation time estimating unit 14 and image superimposing unit 17. A storage unit 23 stores all preset values (e.g. a required transit dose) to be referred to for operating the respective components.

The various components, besides being realizable by software run by the CPU, may be provided by programmable hardware such as FPGA (Field Programmable Gate Array). As long as the following functions are provided in cooperation with hardware resources, the construction may be provided in various modes, such as by either hardware or software, or partially by software.

Figure 2:
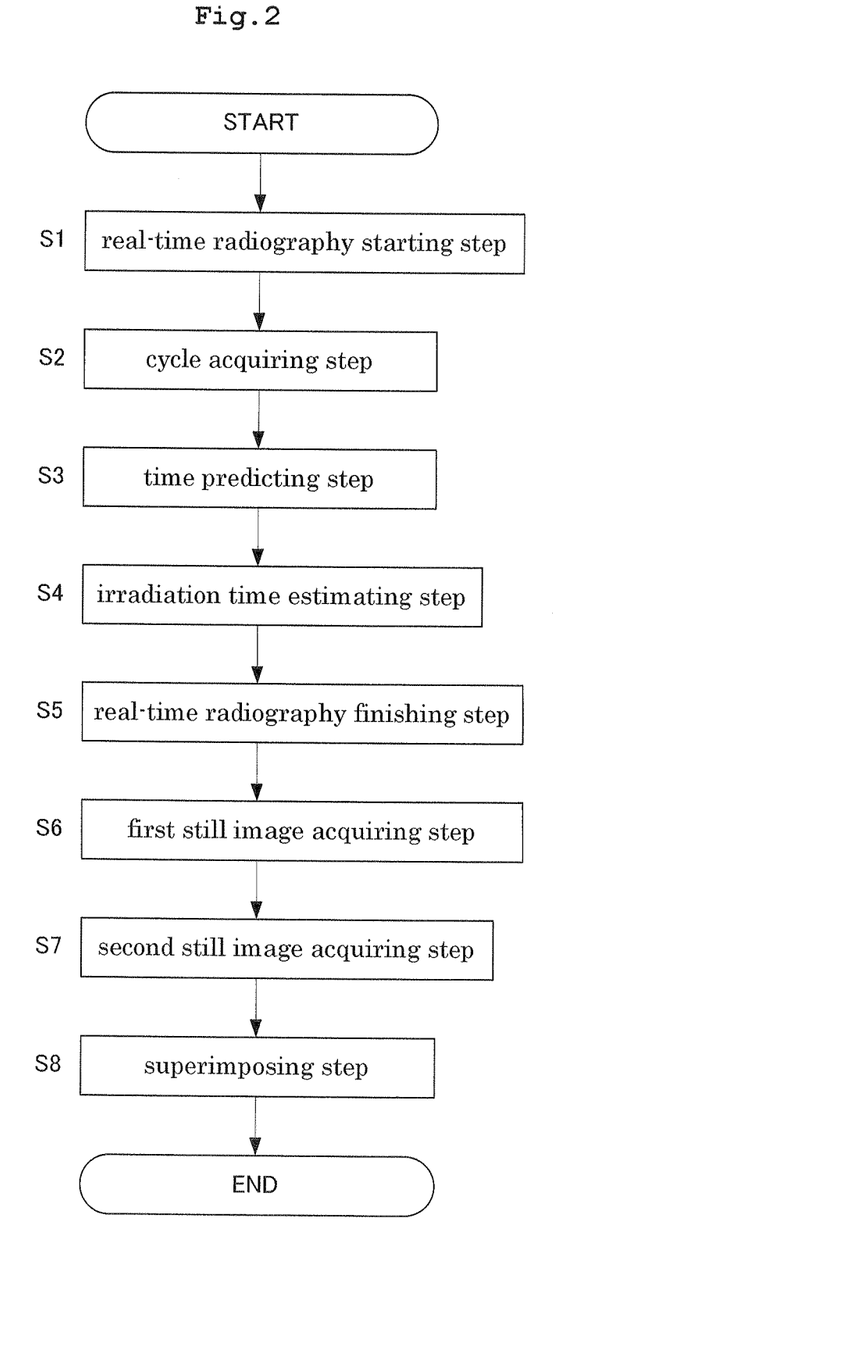
FIG. 2 is a flow chart illustrating operation of the X-ray apparatus according to Embodiment 1.

Operation of this X-ray apparatus 1 will be described. For acquiring a subtraction image with the X-ray apparatus 1 according to Embodiment 1, as shown in FIG. 2, Dynamic image radiography is first started (step S1). A cycle of variations of dynamic parts of the patient M is acquired (step S2). A time when the dynamic parts of the patient M will be in a predetermined state for still image radiography is predicted to acquire a predicted time (step S3). Times of X-ray irradiation required for the still image radiography are estimated (step S4). The steps up to this point constitute a stage prior to the still image radiography, and are executed in order to determine timing of the still image radiography. Subsequently, the Dynamic image radiography is completed (step S5), and a first still image is acquired (step S6). Then, a second still image is acquired (step S7). The still images are superimposed (step S8). Details of each step will be described in order hereinafter.

<Dynamic Image Radiography Starting Step S1>

First, the patient M is placed on the top board 2. When the operator gives instructions through a console 21 to start acquisition of a subtraction image, the X-ray tube controller 6 controls the X-ray tube 3 to emit X-rays intermittently. X-rays are emitted every 15 milliseconds, for example. X-ray beams are emitted in a lower dose at this time than at the time of still image radiography described hereinafter, to reduce the patient's exposure as much as possible. In the real-time radiography, irradiation is carried out with conditions that the X-ray tube 3 is set to a tube voltage, tube current and pulse width of 80 kV, 2 mA and 5 msec, for example.

The X-ray beams emitted from the X-ray tube 3 are transmitted through the patient M to be detected by the FPD 4. The FPD 4 outputs real-time detection data L to the histogram analyzing unit 10. The real-time detection data L at this time is table data presenting a relationship between positions of the FPD 4 and detection values indicating detected intensities of the X-rays. If the detection values are arranged in two dimensions according to the position information on the FPD 4, fluoroscopic images of the patient M will be generated. Based on the real-time detection data L, the histogram analyzing unit 10 acquires histograms H presenting a relationship between frequencies and detection values (see FIG. 3), and outputs the histograms H to the cycle acquiring unit 12.

<Cycle Acquiring Step S2>

The cycle acquiring unit 12 reads from the storage unit 23 an upper limit v1 and a lower limit v2 of the detection values to be used for determination of a lung field. The lungs of the patient M have a property of easily transmitting X-rays, compared with the other parts. That is, the lung field of the patient M is detected by the FPD 4 at certain specific detection values. Using this property, the cycle acquiring unit 12 can find out how the lung field of the patient M will change. Specifically, the cycle acquiring unit 12 acquires an area of a region R in the histograms H present between the upper limit v1 and lower limit v2 of the detection values. The upper limit v1 and lower limit v2 will be described. In practice, the lungs of the patient M are detected by the FPD 4 at similar detection values. The detection values have a certain amount of variation, and are not the same over the entire lung field. It is the upper limit v1 and lower limit v2 that indicate the range of the variation in the detection values. In the real-time radiography, the lungs of the patient M are detected by the FPD 4 at certain detection values between the upper limit v1 and lower limit v2.

Figure 3:
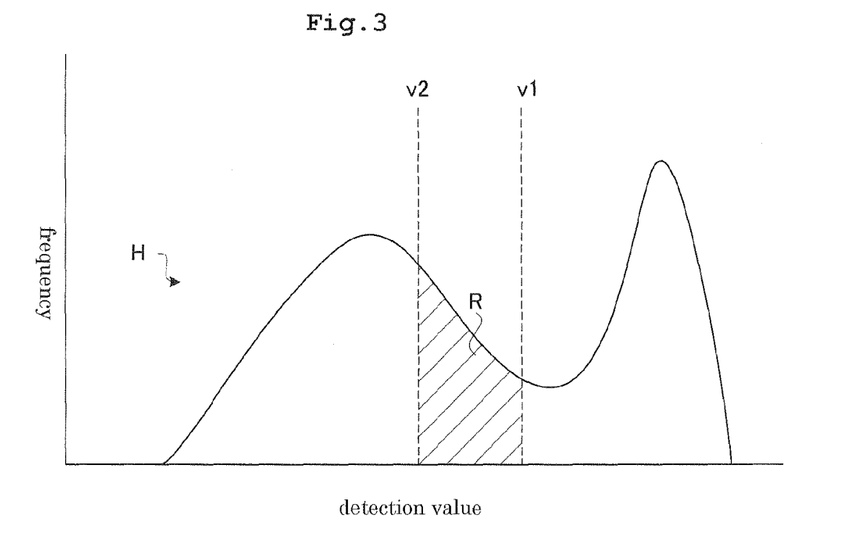
FIG. 3 is a schematic view illustrating operation of the X-ray apparatus according to Embodiment 1.

The cycle acquiring unit 12 calculates the area of region R shown in FIG. 3 whenever the histograms H are outputted, and generates a time course showing temporal variations of the area of region R. By referring to this time course, it is possible to learn the type of cyclicity with which the area of the lung field of the patient M changes over time.

Figure 4:
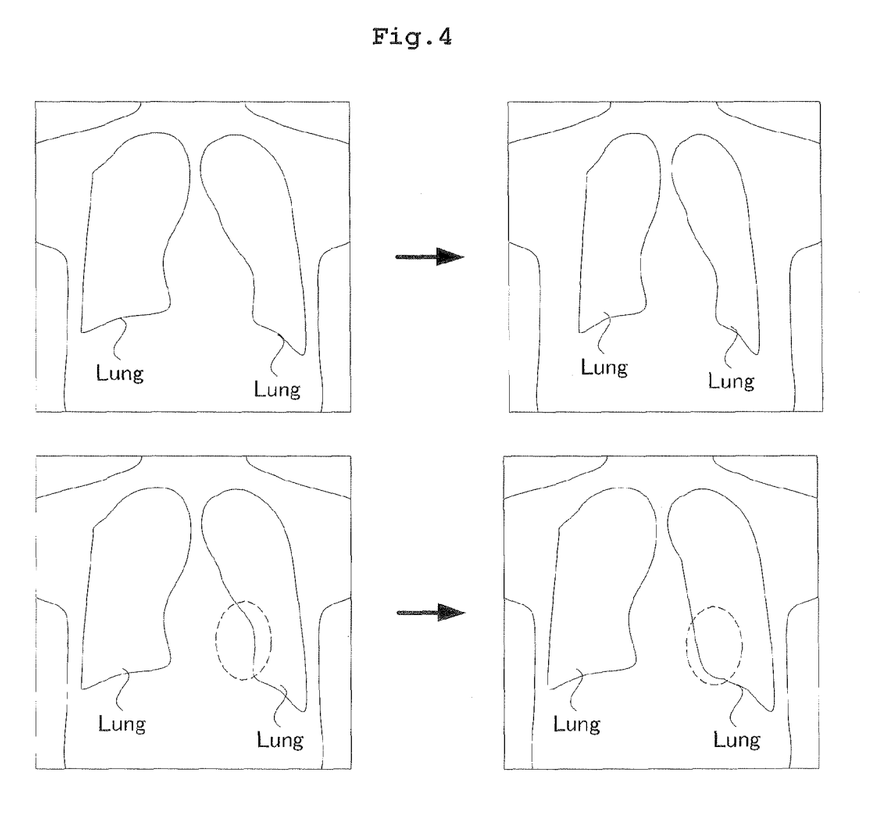
FIG. 4 is a schematic view illustrating operation of the X-ray apparatus according to Embodiment 1.

Cyclic variations of the lungs of the patient M will be described. With respiration of the patient M, the lungs of the patient M will expand and contract (see the upper portion of FIG. 4). As the heart of the patient M pulsates, a portion, adjacent the heart, of the right lung (which is the left lung for the patient) will protract and retract (see the portion surrounded by a dotted line in the lower portion of FIG. 4).

Figure 5:
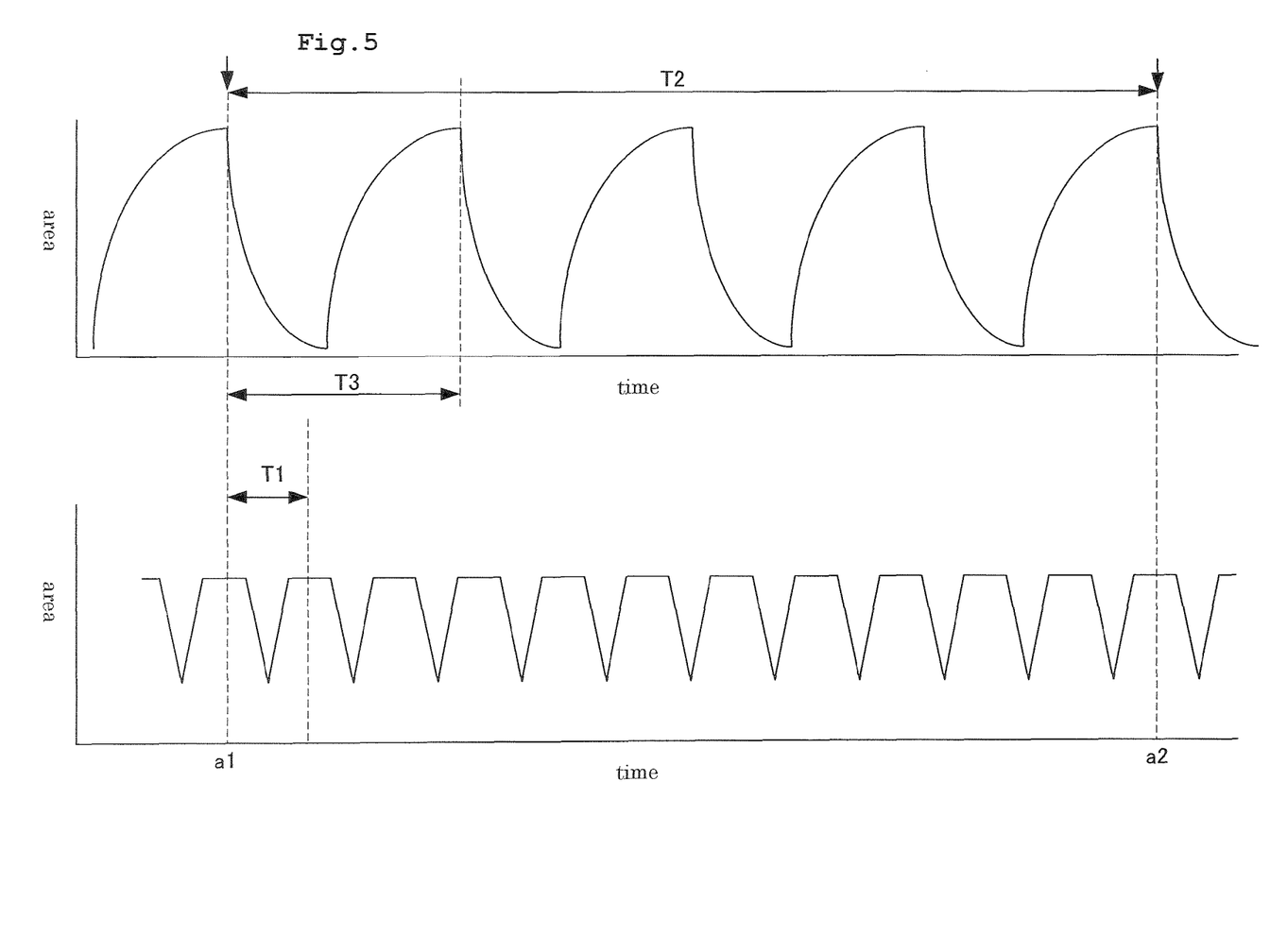
FIG. 5 is a schematic view illustrating operation of the X-ray apparatus according to Embodiment 1.

The time course created by the cycle acquiring unit 12 is a sum of variations in long cycles due to respiration of the patient M shown in the upper portion of FIG. 5 and variations in short cycles due to pulsation of the heart of the patient M shown in the lower portion of FIG. 5. Based on data of this time course, the cycle acquiring unit 12 determines a pulsating cycle T1 and outputs it to the time predicting unit 13. In a specific method for determining the cycle, the cycle acquiring unit 12 sequentially calculates a rate of variations in the lung field area at each point of time, and determines a time required for variations corresponding to one cycle.

It is also possible to acquire a cycle T2 of beats of respiration of the patient M and pulsation of the heart (see FIG. 5). Specifically, the cycle T2 of beats is a period of time from a point of time a1 when the lungs are expanded by inhaling action of the patient M and the lungs expanded also by pulsation of the heart, until a point of time a2 when the respiration and pulsation of the patient M make the same state subsequently. The cycle acquiring unit 12 sets, as one cycle, a period of time from a point of time when the respiration of the patient M is in a specific state and the heartbeat of the patient M is also in a specific state, until a point of time when the respiration of the patient M is in the same state as before and the heartbeat of the patient M is also in the same state as before again. The cycle acquiring unit 12 outputs the time course and cycle T2 of beats to the time predicting unit 13.

<Time Predicting Step S3>

The time predicting unit 13 predicts a time taken until the respiration and heartbeat reach the specific states. If, for example, it is desired to carry out still image radiography when the heart of the patient M is in the most contracted state, specific points of time suited for the purpose will be the times when integral multiples of the cycle T1 elapse after time a1 in FIG. 5. Time a1 is a point of time when the heart is contracted most, but there is also a case where it is desired to carry out still image radiography when the heart is expanded most. Then, the X-ray apparatus 1 can temporally shift the timing of still image radiography. The timing of still image radiography is adjustable by the operator operating the console 21. Consequently, still image radiography can be carried out in the state where the heart of the patient M is expanded most, for example. The time predicting unit 13, upon elapse of a time predicted by itself, will continue predicting one time after another by increasing the integer for multiplying the cycle T1.

When it is desired to carry out still image radiography in the state where the lungs of the patient M are expanded most by both the heartbeat and respiration, for example, the time predicting unit 13 will predict times when integral multiples of the beat cycle T2 elapse after time a1 in FIG. 5.

<Irradiation Time Estimating Step S4>

The real-time detection data L outputted from the FPD 4 is sent also to the irradiation time estimating unit 14. The irradiation time estimating unit 14 refers to detection values of the real-time detection data L, and determines a period of time for which X-rays should be emitted in the still image radiography. Specifically, the irradiation time estimating unit 14 first reads from the storage unit 23 output intensities of the X-ray tube 3 for the real-time radiography and still image radiography, and the required transit dose which is an X-ray dose required for exposure in the still image radiography. The required transit dose is a dose of X-rays transmitted through the patient M and incident on the FPD 4, which specifically is as follows. In the still image radiography, unless a proper dose of X-rays is incident on the FPD 4, only an underexposed or overexposed still image will be obtained. The required transit dose means a dose of X-rays incident on the FPD 4 which is the quantity suitable for radiography in the still image radiography. When, for example, the patient M has a large thickness, a reduced dose of X-rays is transmitted through the patient M, and therefore the still image radiography tends to be carried out with a dose less than the required transit dose. In order to avoid this, the X-ray irradiation time must be extended. Thus, a proper irradiation time for the still image radiography varies with the physique of the patient M.

An irradiation time suitable for the still image radiography is estimated by the irradiation time estimating unit 14. The irradiation time estimating unit 14 derives, from the output intensity of the X-ray tube 3 at the time of real-time radiography and the real-time detection data L, an absorption coefficient indicating how easily radiation is absorbed by the material forming the patient M, and thickness of the patient M. The above absorption coefficient is a qualitative factor indicating an easiness of blocking X-rays, and the patient thickness is a quantitative factor indicating an easiness of blocking X-rays. Therefore, a degree of easiness of the patient M transmitting X-rays can be determined from these factors. Specifically, the irradiation time estimating unit 14 converts the patient M into water, and calculates a water length. The water length means a length of water which, when fluoroscoped, corresponds to the easiness of the patient M blocking X-rays.

Based on the easiness of the patient M blocking X-rays which is numerically expressed by the water length, the irradiation time estimating unit 14 estimates such an irradiation time that the still image radiography will not result in underexposure or overexposure when this patient M is irradiated with X-rays at the output intensity of the X-ray tube 3 (which is a product of a tube voltage and a tube current of the X-ray tube 3, and will hereinafter be called the predetermined intensity) for the still image radiography. Specifically, the irradiation time estimating unit 14 simulates a case of irradiating a calculated length of water with X-rays at the predetermined intensity, to find out how long the irradiation with X-rays should be continued for the dose of X-rays reaching the FPD 4 to equal the required transit dose. In this way, an irradiation time for fluoroscopy is estimated.

In fact, still image acquisition is carried out twice, and different tube voltages are set to the X-ray tube 3 between the first image and second image, and hence different output intensities. Then, the irradiation time estimating unit 14 estimates an irradiation time for acquiring each of the two still images, to obtain estimated irradiation times s1 and s2. Since the output of the X-ray tube 3 is higher for the first radiography than the second, the estimated time for the first radiography is correspondingly shorter. In the still image radiography, irradiation is carried out with the tube voltage and tube current of the X-ray tube 3 and the irradiation time, i.e. pulse width conditions, set to 80 kV, 100 mA and 80 msec.

<Dynamic Image Radiography Finishing Step S5>

When the operator gives instructions through the console 21 for a shift to the still image radiography mode, the X-ray tube controller 6 will stop the emission of X-rays from the X-ray tube 3.

<First Still Image Acquiring Step S6>

Figure 6:
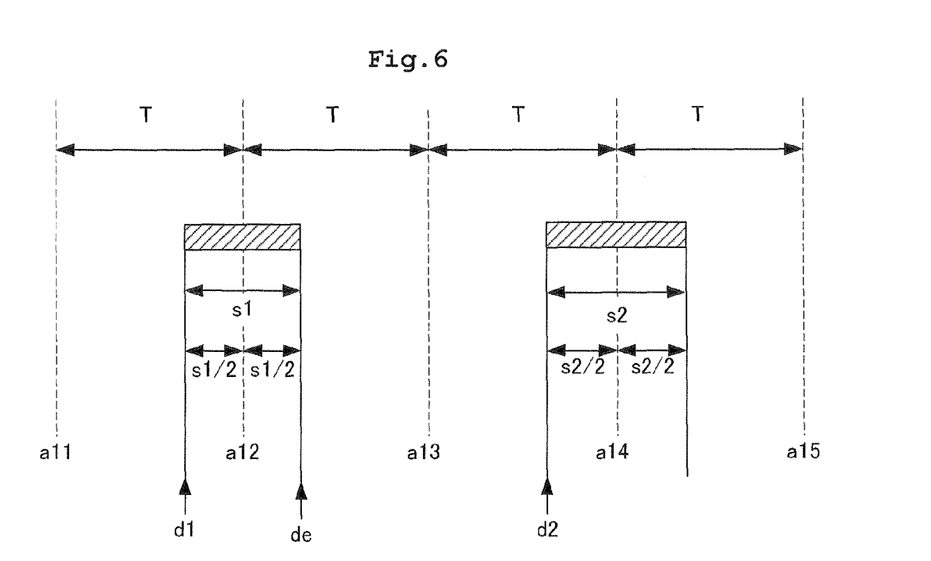
FIG. 6 is a schematic view illustrating operation of the X-ray apparatus according to Embodiment 1.

Next, the still image radiography is started in earnest. Points of time p1, p2, p3 and so on predicted by the time predicting unit 13 and estimated irradiation times s1 and s2 obtained by the irradiation time estimating unit 14 have been outputted to the X-ray tube controller 6. Estimated irradiation time s1 is an irradiation time for the first radiography, and estimated irradiation time s2 an irradiation time for the second radiography. The X-ray tube controller 6 reads control information (the tube current, tube voltage and pulse width) from the storage unit 23 for controlling the X-ray tube 3 for the first still image radiography. As shown in FIG. 6, the X-ray tube 3 is controlled to start emitting X-rays at time d1 which goes back by a half of estimated irradiation time s1 from a certain predicted time a12. The intensity of X-rays outputted from the X-ray tube 3 for the first still image radiography is the same as the output intensity of the X-ray tube 3 used when the irradiation time estimating unit 14 obtained estimated irradiation time s1.

The X-ray tube 3 emits still X-rays with predetermined tube current, tube voltage and pulse width toward the patient M. The phototimer 9 successively calculates a cumulative value of doses of X-rays incident on itself, and when the cumulative value reaches the required transit dose, instructs the X-ray tube controller 6 to end the X-ray emission.

The X-rays emitted from the X-ray tube 3 and transmitted through the patient M fall on the FPD 4. The FPD 4 detects the X-rays, and outputs quiescence detection data S to the image generating unit 11. Based on this data, the image generating unit 11 generates a first still image P1.

The phototimer 9 instructs an end of the X-ray emission according to the required transit dose read from the storage unit 23. As shown in FIG. 6, the time from time d1 to the end of the X-ray emission is equal to the estimated irradiation time s1 obtained in advance by the irradiation time estimating unit 14. Therefore, the point of time right at the middle of the X-ray emission time is the predicted time a12. At the predicted time a12, the state of heartbeat is the same as the state at time a1 shown in FIG. 5.

Depending on the type of examination, the still image radiography may be carried out by installing a additional filter, which can remove long wavelength components of X-ray beams, on an X-ray emitting portion of the X-ray tube 3 after completion of the real-time radiography mode. Operation of the X-ray tube controller 6 in this case will be described. The X-ray tube controller 6 multiplies the estimated irradiation times by a predetermined coefficient, to extend the estimated irradiation times. In this way, even if the X-ray beams become weaker due to the presence of the additional filter, this weakness is complemented to enable the still image radiography. The coefficient for multiplying the estimated irradiation times is stored in the storage unit 23.

<Second Still Image Acquiring Step S7>

Subsequently, the second still image radiography is carried out. The X-ray tube controller 6 reads control information (the tube current, tube voltage and pulse width) from the storage unit 23 for controlling the X-ray tube 3 for the second still image radiography. As shown in FIG. 6, the X-ray tube 3 is controlled to start emitting X-rays at time d2 which goes back by a half of estimated irradiation time s2 from a certain predicted time a14. The intensity of X-rays outputted from the X-ray tube 3 for the second still image radiography is the same as the output intensity of the X-ray tube 3 used when the irradiation time estimating unit 14 obtained estimated irradiation time s2. The intensity of X-rays is lower at this time than at the time of the first still image radiography.

The X-ray tube 3 emits still X-rays with predetermined tube voltage and tube current toward the patient M. The phototimer 9 successively calculates a cumulative value of doses of X-rays incident on itself, and when the cumulative value reaches the required transit dose, instructs the X-ray tube controller 6 to end the X-ray emission. The X-rays emitted from the X-ray tube 3 and transmitted through the patient M fall on the FPD 4. The FPD 4 detects the X-rays, and outputs quiescence detection data S to the image generating unit 11. Based on this data, the image generating unit 11 generates a second still image P2.

The phototimer 9 instructs an end of the X-ray emission according to the required transit dose read from the storage unit 23. As shown in FIG. 6, the time from time d2 to the end of the X-ray emission is equal to the estimated irradiation time s2 obtained in advance by the irradiation time estimating unit 14. Therefore, the point of time right at the middle of the X-ray emission time is the predicted time a14. At the predicted time a14, the state of heartbeat is the same as the state at time a1 shown in FIG. 5 and at predicted time a12 shown in FIG. 6. The first radiography and second radiography are carried out for equal times before and after the predicted times, thereby to minimize blurring of the images under the influence of minute beating motions of the heart taking place during the radiographing periods. Thus, the states of heartbeat of the patient M reflected on the first still image P1 and second still image P2 are in agreement.

The dose of radiation usually is larger for the still image radiography than for the real-time radiography. With the phototimer 9 instructing ends of X-ray emission in the still image radiography, the X-ray apparatus provided guarantees a high level of safety.

<Superimposing Step S8>

The first still image P1 and second still image P2 are outputted to the image superimposing unit 17. The image superimposing unit 17 subtracts the second still image P2 from the first still image P1 to acquire a subtraction image emphasizing bone tissue or soft tissue of the patient M. A subtraction image emphasizing a different tissue can be acquired by acquiring a difference between the still images P1 and P2 after carrying out a predetermined tone correction thereof. Since the states of heartbeat of the patient M reflected on the first still image P1 and second still image P2 are in agreement, the two images can be combined without shifting, thereby to acquire a subtraction image with no blur. This subtraction image is displayed on the display unit 22, to complete the operation of the X-ray apparatus 1 according to this invention.

According to the construction in Embodiment 1, as described above, real-time radiography is carried out first to acquire real-time detection data L, and then still image radiography for diagnosis is carried out to acquire quiescence detection data S. The real-time radiography is carried out as preparation to determine radiographic conditions for the still image radiography. In the real-time radiography, a point of time when the dynamic parts of the patient M will be in a predetermined state is predicted, and X-ray irradiation times for the still image radiography are estimated. The point of time is predicted by the time predicting unit 13. The irradiation times are estimated by the irradiation time estimating unit 14.

In the still image radiography in Embodiment 1, X-ray irradiation is started at a time earlier than a predicted point of time by a half of an estimated irradiation time. By choosing this process, the X-ray irradiation at the time of still image radiography ends at a point of time when the dynamic parts of the patient M are in a predetermined state. With such still image radiography repeated a plurality of times, the heart of the patient M will be reflected in the same shape on the still images acquired. These images may be superimposed together to acquire a subtraction image without a blur due to movement of the heart of the patient M.

Even if the cyclicities of the lung field and the heart of the patient M are different in Embodiment 1, blurring of the subtraction image is inhibited. That is, a cycle is determined to be a time taken from a point of time when the state of respiration of the patient M is in a specific state and the state of heartbeat of the patient M is in a specific state, to a point of time when the state of respiration of the patient M is in the same specific state as before again and the state of heartbeat of the patient M is in the same specific state as before again. Consequently, whenever still images are picked up, the lung field and the heart are reflected in the same shape and position on the still images.

Embodiment 2

Next, an X-ray apparatus 1 according to Embodiment 2 will be described. The X-ray apparatus according to Embodiment 2 is used for chest radiography and, as distinct from the construction in Embodiment 1, X-rays the chest by emitting a still X-ray beam. This apparatus does not generate a subtraction image. Therefore, in Embodiment 2, the image superimposing unit 17 shown in FIG. 1 is dispensable. The other aspects of the construction are the same as those of the construction in Embodiment 1 described with reference to FIG. 1.

Figure 7:
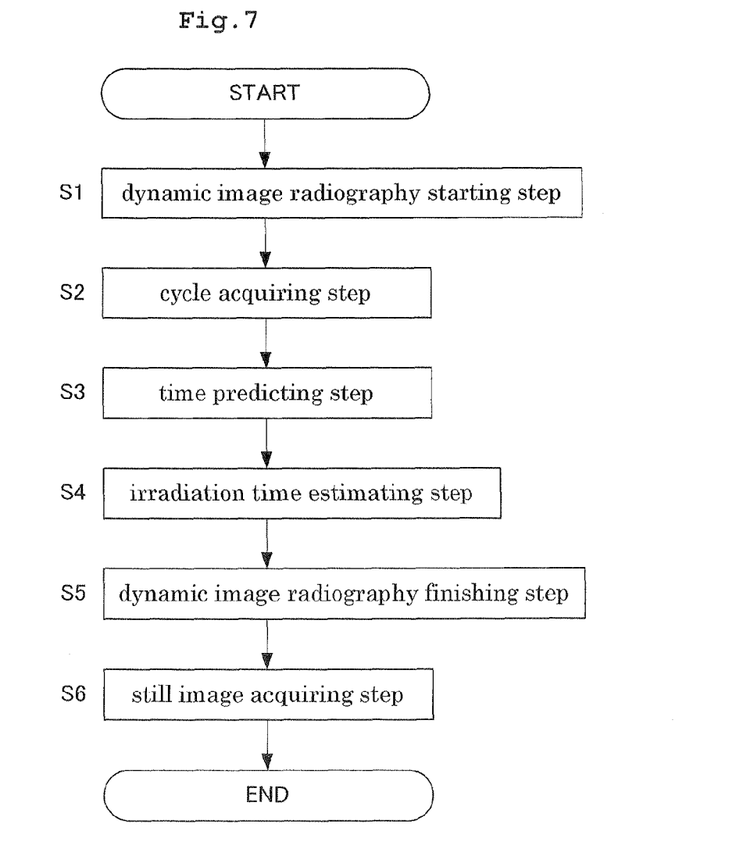
FIG. 7 is a flow chart illustrating operation of an X-ray apparatus according to Embodiment 2.

Operation of this X-ray apparatus 1 will be described. For acquiring a still image with the X-ray apparatus 1 according to Embodiment 2, as shown in FIG. 7, dynamic image radiography is first started (step S1). A cycle of variations of the lungs of the patient M is acquired (step S2). A time when the lungs of the patient M will be in a predetermined state for still image radiography is predicted to acquire a predicted time (step S3). A time of X-ray irradiation required for the still image radiography is estimated (step S4). The steps up to this point constitute a stage prior to the still image radiography, and are executed in order to determine timing of the still image radiography. Subsequently, the dynamic image radiography is completed (step S5), and a still image is acquired (step S6). Details of each step will be described in order hereinafter. The lungs correspond to the body organ in this invention.

<Dynamic Image Radiography Starting Step S1>

First, the patient M is placed on the top board 2. When the operator gives instructions through the console 21 to start chest radiography, the X-ray tube controller 6 controls the X-ray tube 3 to emit X-rays intermittently. X-rays are emitted every 15 milliseconds, for example. X-ray beams are emitted in a lower dose at this time than at the time of still image radiography described hereinafter, to reduce the patient's exposure as much as possible. In dynamic image radiography, irradiation is carried out with conditions that the X-ray tube 3 is set to a tube voltage, tube current and pulse width of 80 kV, 2 mA and 5 msec, for example.

The X-ray beams emitted from the X-ray tube 3 are transmitted through the patient M to be detected by the FPD 4. The FPD 4 outputs real-time detection data L to the histogram analyzing unit 10. The real-time detection data L at this time is table data presenting a relationship between positions of portions in the FPD 4 and detection values indicating detected intensities of the X-rays. If the detection values are arranged in two dimensions according to the position information on the FPD 4, fluoroscopic images of the patient M will be generated. Based on the real-time detection data L, the histogram analyzing unit 10 acquires histograms H presenting a relationship between frequencies and detection values (see FIG. 3), and outputs the histograms H to the cycle acquiring unit 12.

<Cycle Acquiring Step S2>

The cycle acquiring step S2 is the same as in the foregoing Embodiment 1 and will not be described again. The cycle acquiring unit 12 determines how the lung field of the patient M changes, using the upper limit v1 and lower limit v2.

Thus, the time course created by the cycle acquiring unit 12 is a sum of variations in long cycles due to respiration of the patient M shown in the upper portion of FIG. 5 and variations in short cycles due to pulsation of the heart of the patient M shown in the lower portion of FIG. 5. Based on data of this time course, the cycle acquiring unit 12 determines a breathing cycle T3 and outputs it to the time predicting unit 13. In a specific method for determining the cycle, the cycle acquiring unit 12 sequentially calculates a rate of variation in the lung field area each time, and determines a time required for variations corresponding to one cycle. The cycle acquiring unit 12 may acquire the cycle T2 of beats as described hereinbefore.

<Time Predicting Step S3>

The time predicting unit 13 predicts a time taken until the respiration and heartbeat reach the specific states. If, for example, it is desired to carry out still image radiography when the lungs of the patient M are in the most expanded state, specific points of time suited for the purpose will be the times when integral multiples of the cycle T3 elapse after time a1 in FIG. 5. Time a1 is a point of time when the lungs of the patient M are expanded most, but there is also a case where it is desired to carry out still image radiography when the lungs of the patient M are contracted most. Then, the X-ray apparatus 1 can temporally shift the timing of still image radiography. The timing of still image radiography is adjustable by the operator operating the console 21. Consequently, still image radiography can be carried out in the state where the lungs of the patient M are contracted most, for example. The time predicting unit 13, upon elapse of a time predicted by itself, will continue predicting one time after another by increasing the integer for multiplying the cycle T3.

When it is desired to carry out still image radiography in the state where the lungs of the patient M are expanded most by both the heartbeat and respiration, for example, the time predicting unit 13 will predict times when integral multiples of the beat cycle T2 elapse after time a1 in FIG. 5.

<Irradiation Time Estimating Step S4>

The irradiation time estimating step S4 is the same as in the foregoing Embodiment 1 and will not be described again. The irradiation time estimating unit 14 derives a water length from the output intensity of the X-ray tube 3 at the time of dynamic image radiography and real-time detection data L. This water length has already been described. The irradiation time estimating unit 14 estimates a proper irradiation time based on the water length and the control information for controlling the X-ray tube 3.

<Dynamic Image Radiography Finishing Step S5>

When the operator gives instructions through the console 21 for a shift to the still image radiography mode, the X-ray tube controller 6 will stop the emission of X-rays from the X-ray tube 3.

<Still Image Acquiring Step S6>

Next, the still image radiography is started in earnest. Points of time p1, p2, p3 and so on predicted by the time predicting unit 13 and estimated irradiation time s1 obtained by the irradiation time estimating unit 14 have been outputted to the X-ray tube controller 6. Estimated irradiation time s1 is an irradiation time for the still image radiography. The X-ray tube controller 6 reads control information (the tube current, tube voltage and pulse width) from the storage unit 23 for controlling the X-ray tube 3 for the first still image radiography. As shown in FIG. 6, the X-ray tube 3 is controlled to start emitting X-rays at time d1 which goes back by a half of estimated irradiation time s1 from a certain predicted time a12. The intensity of X-rays outputted from the X-ray tube 3 for the still image radiography is the same as the output intensity of the X-ray tube 3 used when the irradiation time estimating unit 14 obtained estimated irradiation time s1.

The X-ray tube 3 emits still X-rays with predetermined tube current, tube voltage and pulse width toward the patient M. The phototimer 9 successively calculates a cumulative value of doses of X-rays incident on itself, and when the cumulative value reaches the required transit dose, instructs the X-ray tube controller 6 to end the X-ray emission.

That is, the phototimer 9 instructs an end of the X-ray emission according to the required transit dose read from the storage unit 23. As shown in FIG. 6, the time from time d1 to the end of the X-ray emission is equal to the estimated irradiation time s1 obtained in advance by the irradiation time estimating unit 14. Therefore, the point of time at the middle of the X-ray emission time is the predicted time a12. At the predicted time a12, the state of respiration of patient M is the same as the state at time a1 shown in FIG. 5. By emitting X-rays for equal times before and after the predicted time as described above, it is possible to minimize the influence of minute motions of the patient M on the state at the predicted time desirable for radiography.

The X-rays emitted from the X-ray tube 3 and transmitted through the patient M fall on the FPD 4. The FPD 4 detects the X-rays, and outputs quiescence detection data S to the image generating unit 11. Based on this data, the image generating unit 11 generates a still image P1. The still image P1 acquired in this way is displayed on the display unit 22, to complete the operation of the X-ray apparatus 1 according to this invention.

Depending on the type of examination, the still image radiography may be carried out by installing a additional filter, which can remove long wavelength components of X-ray beams, on an X-ray emitting portion of the X-ray tube 3 after completion of the dynamic image radiography mode. Operation of the X-ray tube controller 6 in this case will be described. The X-ray tube controller 6 multiplies the estimated irradiation times by a predetermined coefficient, to extend the estimated irradiation times. In this way, even if the X-ray beams become weaker due to the presence of the additional filter, this weakness is complemented to enable the still image radiography. The coefficient for multiplying the estimated irradiation times is stored in the storage unit 23.

The dose of radiation usually is larger for still image radiography than for dynamic image radiography. With the phototimer 9 instructing ends of X-ray emission in the still image radiography, the X-ray apparatus provided guarantees a high level of safety.

This invention is not limited to the foregoing construction, but may be modified as follows:

(1) According to the construction in Embodiment 1, the cycle acquiring unit 12 derives a cycle from the time course of the area of the lung field. This invention is not limited to this. A cycle may be derived from a time course of the area of the heart instead of the lung field.

(2) The construction in each embodiment includes the histogram analyzing unit 10, but this unit may be omitted. That is, the cycle acquiring unit 12 may count the number of detection values, which are below a certain upper limit and above a certain lower limit, among the real-time detection data L, and regard it as the area of the lung field. These upper limit and lower limit are stored in the storage unit 23.

(3) A cycle may be obtained using a dynamic image outputted from the image generating unit 11 in each embodiment based on the real-time detection data L. That is, the cycle acquiring unit 12 may detect a mass of similar pixel values reflected in a frame of the dynamic image, and obtain area variations, noting that the mass is the lung field, thereby to obtain a cycle. In this case, a cycle may be derived from variations in the shape of the mass or variations in its position, instead of obtaining an area.

Figure 8:
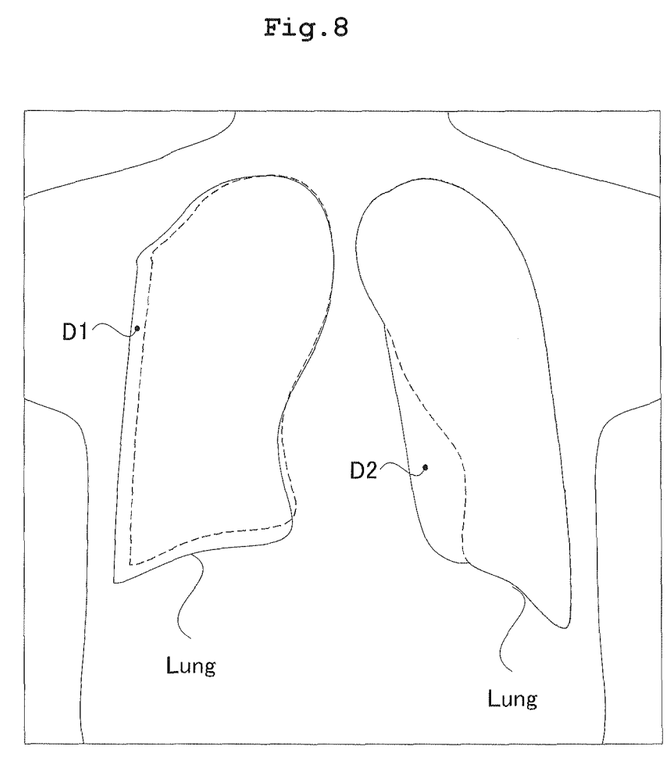
FIG. 8 is a schematic view illustrating a construction according to a modification of this invention.

(4) The cycle acquiring unit 12 in each embodiment may obtain a cycle by recognizing cyclic variations of a specific detection value among the real-time detection data L. The specific detection value referred to at this time, desirably, is a detection value of D1, as shown in FIG. 8, which is located peripherally of a lung, among the real-time detection data L. Similarly, it is desirable if it is a detection value of D2 which is located at a boundary between the heart and a lung, among the real-time detection data L. Since portion D1 belongs to the lung at certain times and does not at other times due to respiration, its detection value changes cyclically. Since portion D2 belongs to the lung at certain times and does not at other times due to heartbeat, its detection value changes cyclically. A cycle may be acquired using this. The cycle acquiring unit 12 can find out a cycle of respiration by portion D1.

(5) In the above construction in each embodiment, the cycle acquiring unit 12 determines a cycle from the time course for one cycle. Instead, a plurality of time courses for one cycle may be acquired, to obtain a cycle independently from each, and a cycle may be determined finally by averaging the plurality of cycles obtained.

(6) In the above construction in each embodiment, the cycle acquiring unit 12 determines a cycle from the time course for one cycle. Instead, a cycle may be determined from a time course for less than one cycle. In this case, a cycle is determined by predicting a time course for one cycle through a wave analysis of the time course.

(7) In the above construction in each embodiment, the cycle acquiring unit 12 is automatically operable. This may be modified to be manually operable. That is, the operator may determine a cycle based on a dynamic image displayed on the display unit 22, and input this to the console 21.

(8) The strut 7 in the above construction in each embodiment may be replaced with a C-arm.

(9) The apparatus in each foregoing embodiment is a medical apparatus. However, this invention is applicable also to an industrial and nuclear apparatus.

(10) X-rays used in each foregoing embodiment are an example of the radiation in this invention. Thus, this invention is applicable also to radiation other than X-rays.

(11) In Embodiment 1 described above, the X-ray irradiation time, i.e. the pulse width, is different between the first radiography and second radiography, that is s1≠s2. The tube current may be adjusted to make s1=s2 while maintaining the value of a product of the tube current and pulse width for each. In that case, it is possible to minimize a difference in minute blurring such as of the heart between the irradiation times for the two radiographic operations.

(12) In Embodiment 1 described above, the points of time at the middle of estimated X-ray irradiation times s1 and s2 are set to agree with the predicted times a12 and a14, respectively. For example, the points of time may be set otherwise than at the middle of estimated X-ray irradiation times s1 and s2 such that the predicted times a12 and a14 agree with the ends of estimated irradiation times s1 and s2. At this time, it is preferable to adjust the tube current as described above, to make estimated irradiation time s1=estimated irradiation time s2.

(13) In the above construction in each embodiment, X-rays are emitted intermittently. However, X-rays may be emitted continuously.

(14) In Embodiment 2 described above, the point of time at the middle of estimated X-ray irradiation time s1 is set to agree with the predicted time a12. For example, the irradiation time s1 may be set as shifted relative to the predicted time a12 such that an end point of time de of estimated irradiation time s1, shown in FIG. 6, and the predicted time a12 are in agreement.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus having a radiation source for emitting radiation, a radiation source control device for instructing the radiation source to emit the radiation, and a radiation detecting device for detecting the radiation, the radiation detecting device outputting real-time detection data when the radiation source emits the radiation intermittently or continuously, and outputting quiescence detection data when the radiation source emits still radiation, the radiographic apparatus comprising:
   a storage device for storing a required transit dose indicating what dose of the radiation transmitted through a patient is required for acquisition of the quiescence detection data;
   a time predicting device for predicting, based on a cycle of variation of a dynamic part which cyclically changes in size in the patient, a point of time when the dynamic part of the patient will be in a predetermined state, as a predicted point of time;
   an irradiation time estimating device for estimating an irradiation time of the radiation at a time of acquiring the quiescence detection data, as an estimated irradiation time, from the real-time detection data and the required transit dose;
   an image generating device for generating still images based on the quiescence detection data; and
   an image superimposing device for superimposing still images picked up at different points of time to create a superimposition image;
   wherein the quiescence detection data is acquired by the radiation source control device controlling the radiation source to start emitting the radiation at a time earlier than the predicted point of time by a predetermined time calculated based on the estimated irradiation time.

2. The radiographic apparatus according to claim 1, further comprising a cycle acquiring device for acquiring the cycle of variation of the dynamic part based on the real-time detection data.

3. The radiographic apparatus according to claim 2 wherein the cycle acquiring device is arranged to acquire the cycle by obtaining, from the real-time detection data, one of an area of the dynamic part, a position of the dynamic part, a shape of the dynamic part, and a radiation detection value in a specific location in an image which belongs to the dynamic part at certain times and does not at other times.

4. The radiographic apparatus according to claim 3, wherein the cycle acquiring device is arranged to acquire the cycle by obtaining variations with time of the dynamic part, and calculating rates of the variations.

5. The radiographic apparatus according to claim 2 wherein the image superimposing device is arranged to create a subtraction image by acquiring a difference between still images picked up under conditions of different outputs of the radiation source.

6. The radiographic apparatus according to claim 2 wherein the dynamic part of the patient is variable by heartbeat.

7. The radiographic apparatus according to claim 6, wherein the dynamic part of the patient comprises the lungs.

8. The radiographic apparatus according to claim 6, wherein the dynamic part of the patient comprises the heart.

9. The radiographic apparatus according to claim 2 wherein the cycle acquiring device is arranged to determine the cycle to be a time taken from a point of time when a state of respiration of the patient is in a specific state and a state of heartbeat of the patient is in a specific state, to at point of time when the state of respiration of the patient is in the same specific state as before and the state of heartbeat of the patient is in the same specific state as before.

10. The radiographic apparatus according to claim 1 wherein the image superimposing device is arranged to create a subtraction image by acquiring a difference between still images picked up under conditions of different outputs of the radiation source.

11. The radiographic apparatus according to claim 1 further comprising a histogram analyzing device for carrying out a histogram analysis of the real-time detection data;
   wherein the cycle acquiring device is arranged to acquire the cycle by comparing histograms sequentially outputted from the histogram analyzing device.

12. The radiographic apparatus according to claim 1 wherein the dynamic part of the patient is variable by heartbeat.

13. The radiographic apparatus according to claim 12, wherein the dynamic part of the patient comprises the lungs.

14. The radiographic apparatus according to claim 12, wherein the dynamic part of the patient comprises the heart.

15. The radiographic apparatus according to claim 1 wherein the cycle acquiring device is arranged to determine the cycle to be a time taken from a point of time when a state of respiration of the patient is in a specific state and a state of heartbeat of the patient is in a specific state, to a point of time when the state of respiration of the patient is in the same specific state as before and the state of heartbeat of the patient is in the same specific state as before.

16. A radiographic apparatus having it radiation source for emitting radiation to a patient, a radiation source control device for instructing the radiation source to emit the radiation, and a radiation detecting device for detecting the radiation transmitted through the patient, and outputting detection data, the radiographic apparatus comprising:
   a cycle acquiring device for detecting, cyclic variations in size of a body organ of the patient;
   wherein the radiation source is arranged to emit the radiation by determining a point of time for starting emission of the radiation based on a cycle detected by the cycle acquiring device;

the radiation detecting device is arranged to output real-time detection data when the radiation source emits the radiation intermittently or continuously; and the cycle acuiring device is arranged to acquire a cycle of variations of the body organ based on the real-time detection data.

17. The radiographic apparatus according to claim 16 further comprising a histogram analyzing device for carrying out a histogram analysis of the real-time detection data;

wherein the cycle acquiring device is arranged to acquire the cycle by comparing histograms sequentially outputted from the histogram analyzing device.

18. The radiographic apparatus according to claim 16 further comprising an image generating device for generating images based on the detection signals;

wherein the cycle acquiring device is arranged to acquire the cycle by obtaining, from the real-time detection data, one of an area of the body organ, a position of the body organ, a shape of the body organ, and a radiation detection value in a location in an image which belongs to the body organ at certain times and does not at other times.

19. The radiographic apparatus according to claim 18, wherein the cycle acquiring device is arranged to acquire the cycle by obtaining variations with time of the lungs of the patient, and calculating rates of the variations.

20. The radiographic apparatus according to claim 16 wherein the radiographic apparatus is constructed for radiographing one of the chest and the abdomen of the patient.

* * * * *